(12) United States Patent
Arehart et al.

(10) Patent No.: US 8,158,155 B2
(45) Date of Patent: Apr. 17, 2012

(54) ODOR CONTROL CELLULOSE-BASED GRANULES

(75) Inventors: Kelly D. Arehart, Roswell, GA (US); Franz Aschenbrenner, Kastl (DE); Annaïg Gaël Della Monta, Forchheim (DE)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1152 days.

(21) Appl. No.: 12/004,148

(22) Filed: Dec. 20, 2007

(65) Prior Publication Data

US 2009/0163888 A1    Jun. 25, 2009

(51) Int. Cl.
  *A61K 9/14*    (2006.01)
(52) U.S. Cl. .................................................. 424/489
(58) Field of Classification Search .................. None
  See application file for complete search history.

(56) References Cited

U.S. PATENT DOCUMENTS

| | | | |
|---|---|---|---|
| 3,794,034 A | 2/1974 | Jones, Sr. | |
| 4,842,593 A | 6/1989 | Jordan et al. | |
| 5,480,636 A * | 1/1996 | Maruo et al. | 424/76.21 |
| 6,852,904 B2 | 2/2005 | Sun et al. | |
| 2006/0008442 A1 * | 1/2006 | MacDonald et al. | 424/76.1 |
| 2006/0229580 A1 | 10/2006 | Raidel et al. | |
| 2006/0233869 A1 * | 10/2006 | Looney et al. | 424/443 |
| 2007/0100304 A1 * | 5/2007 | Fell et al. | 604/359 |
| 2011/0009259 A1 * | 1/2011 | Innerlohinger et al. | 502/402 |

FOREIGN PATENT DOCUMENTS

| | | |
|---|---|---|
| EP | 0046533 B1 | 11/1984 |
| WO | WO 2006/048280 | 5/2006 |

* cited by examiner

*Primary Examiner* — Johann Richter
*Assistant Examiner* — Thor Nielsen
(74) *Attorney, Agent, or Firm* — Randall W. Fieldhack

(57) ABSTRACT

A cellulose-based granule that functions as a carrier vehicle for an odor control agent is described. The granule has a relatively porous substrate body having a high-surface area of at least about 200 m$^2$/gram, and metal-modified silica particles either adhered to or encapsulated within the cellulose-based substrate. Each of the metal-modified particles has adsorbed metallic ions that are adapted to bind a molecule of a gaseous compound, an odorous compound, or combinations thereof. The odor control granule is free-flowing (i.e., do not exhibit a tendency to agglomerate to each other) and exhibit powder-like characteristics, wherein the granules have an average powder density of 30 to 600 g/l according to DIN 53,468.

36 Claims, 4 Drawing Sheets

ODOR CONTROL CELLULOSE-BASED GRANULES

FIELD OF INVENTION

The present invention relates to an odor control product and delivery mechanism or a method for using in a product. In particular, the invention relates to a porous cellulose-based carrier containing an active, predetermined amount of metal-modified silica components

BACKGROUND

Over the years, many attempts have been made to formulate an effective odor removal system and various consumer products are available for combating odiferous compounds. Some products are designed to cover up odors by emitting stronger, more dominant scents, such as may be found in scented air freshener sprays and candles. Another way to combat odiferous compounds, including ammonia, methyl mercaptan, trimethylamine, and other various sulfides and amines, is to remove these compounds from a medium by using deodorizing agents that diminish the presence of the odiferous compounds in the environment.

Activated charcoal and sodium bicarbonate are two compounds commonly used to absorb odors. The deodorizing ability of activated charcoal, however, varies based on the carbon source and the activation method and can have a low deodorizing ability, particularly for ammonia or when in the presence of moisture. Further, the black color of charcoal detracts from what consumer desire as aesthetically pleasing characteristics in otherwise white colored products. Sodium bicarbonate, and other white-colored odor absorbents such as silica gel and zeolites, are generally less effective deodorizers than activated charcoal and are therefore are less desirable to use.

Titanium oxide particles, such as taught in U.S. Pat. No. 5,480,636 issued to Maruo et al., are also useful in removing a few odors such as ammonia. U.S. Pat. No. 5,480,636 teaches adding zinc oxy or silicon oxy compounds to the titanium oxide to broaden the titanium oxide deodorizing capabilities. This approach, however, is limited by the photocatalytic nature of the titanium dioxide which requires light in order to convert odorous compounds into non-odorous compounds and as disclosed in U.S. Pat. No. 5,480,636, the titanium oxide compound's inability to function in aqueous solutions.

Within the odor control technology area, many have tried to improve odor control either by means of developing novel odor-absorbent compounds or through optimizing delivery of known odor control agents. A need exists for an odor removal compound and a delivery mechanism for said compound that is effective in both dry and moist environments. The delivery mechanism should be generate effective for odor removal either as a stand-alone substance that can be easily applied to various surfaces and materials or in various industrial and consumer products.

SUMMARY OF THE INVENTION

Functionalized, porous, cellulose-based granules can serve as a novel delivery mechanism for certain odor-absorbent chemistries. Powder-like granules are made from discrete, interwoven cellulose strands that serve as a carrier vehicle or substrate for metal-modified silica particles, which maintain absorbent efficacy, as well as provide flexibility in fabrication into different kinds of products and delivery processes for various uses. The functional granules can be broadly applicable to odor control products.

The invention incorporates high-surface area, metal-modified silica materials by means of either physical adhesion or encapsulation in a cellulose-based carrier substrate. The carrier substrate is useful in neutralizing or removing gases and/or odorous compounds. The high surface area material can be nanoparticles coated with metal ions that can bind with gas molecules and/or odorous compounds. The substrate containing the modified high surface area materials can be employed as a free-standing odor absorbent in a powder form. Alternatively, since the cellulose-based granules tend to be free-flowing, even when wet from exposure to a liquid, the granules can be loaded in self-contained pouches that allow air-flow or sprinkled loosely in packaging, for use as a general absorbent, without the mess or other problems associated with conventional ink or liquid-based delivery vehicles. The granules can be incorporated into various industrial and consumer products including absorbent articles, air and water filters, household cleaners, fabrics, and paper towels.

The invention, in another aspect, relates to an article of manufacture, such absorbent articles that are used for personal care products. The odor-control carrier substrate can be incorporated via a dosed delivery, similar to current industry methods employed to dosing superabsorbent materials into diapers or feminine hygiene products, an adult incontinence product, a protective garment, or used directly in a raw particle form for household applications like carpet or garbage odor control. The fluffy, granule nature of the carrier vehicle permits one to provide a predetermined or specified amount of odor control material into the products. The cellulose-based granule particles can be broadly applicable to odor control products, an air-freshener medium or package, air-filter medium. The medium can have the cellulose-based carrier substrates located in interstitial spaces of a nonwoven fabric web. A manufacturer can deposit a precise amount of activated odor control material accurately on locations of a substrate or incorporated the material within like products.

DETAILED DESCRIPTION OF THE INVENTION

Section I—Description

Figure 1:
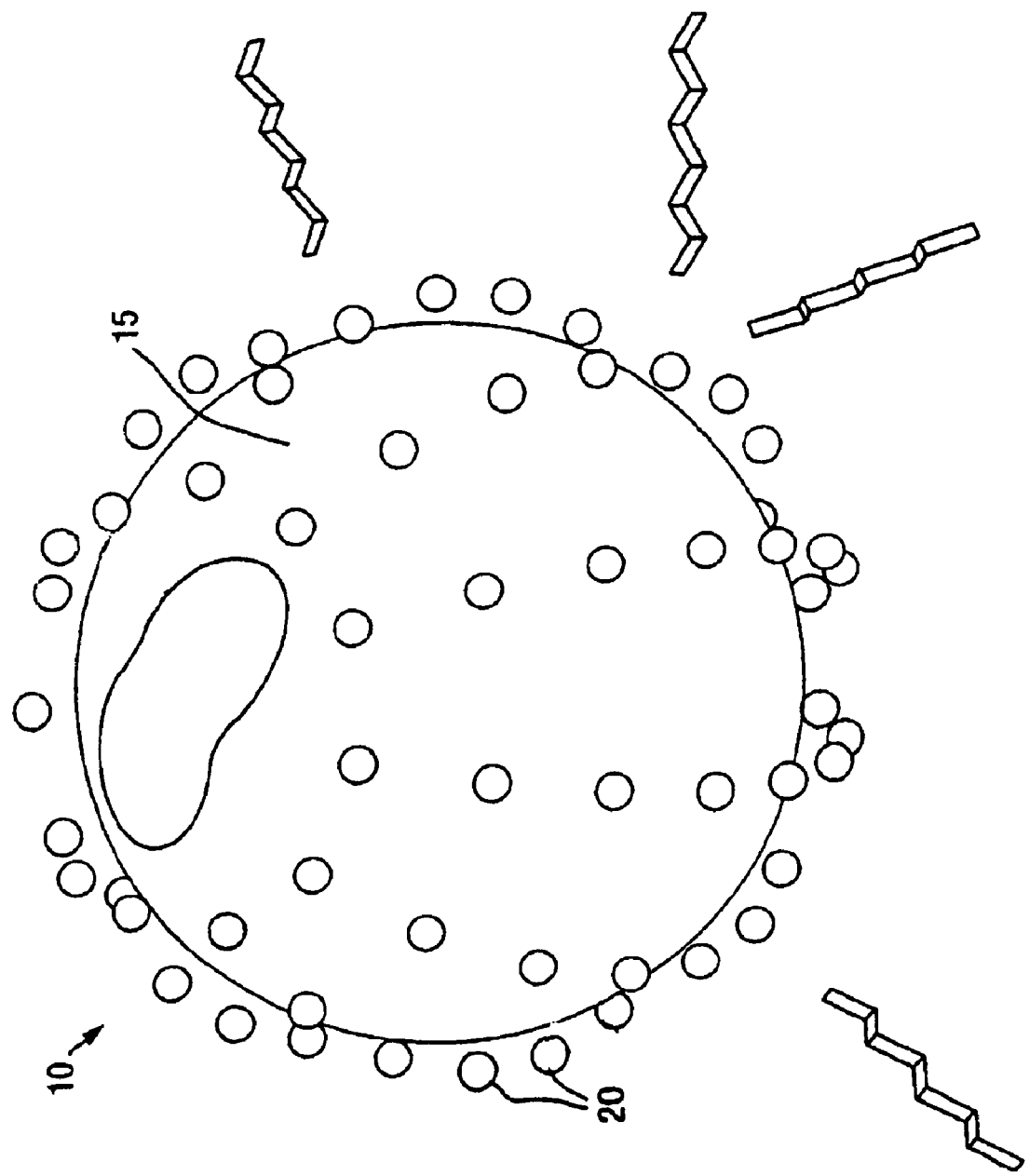
FIG. 1 is a drawing of a metal-ion modified nanoparticle.
Figure 2:
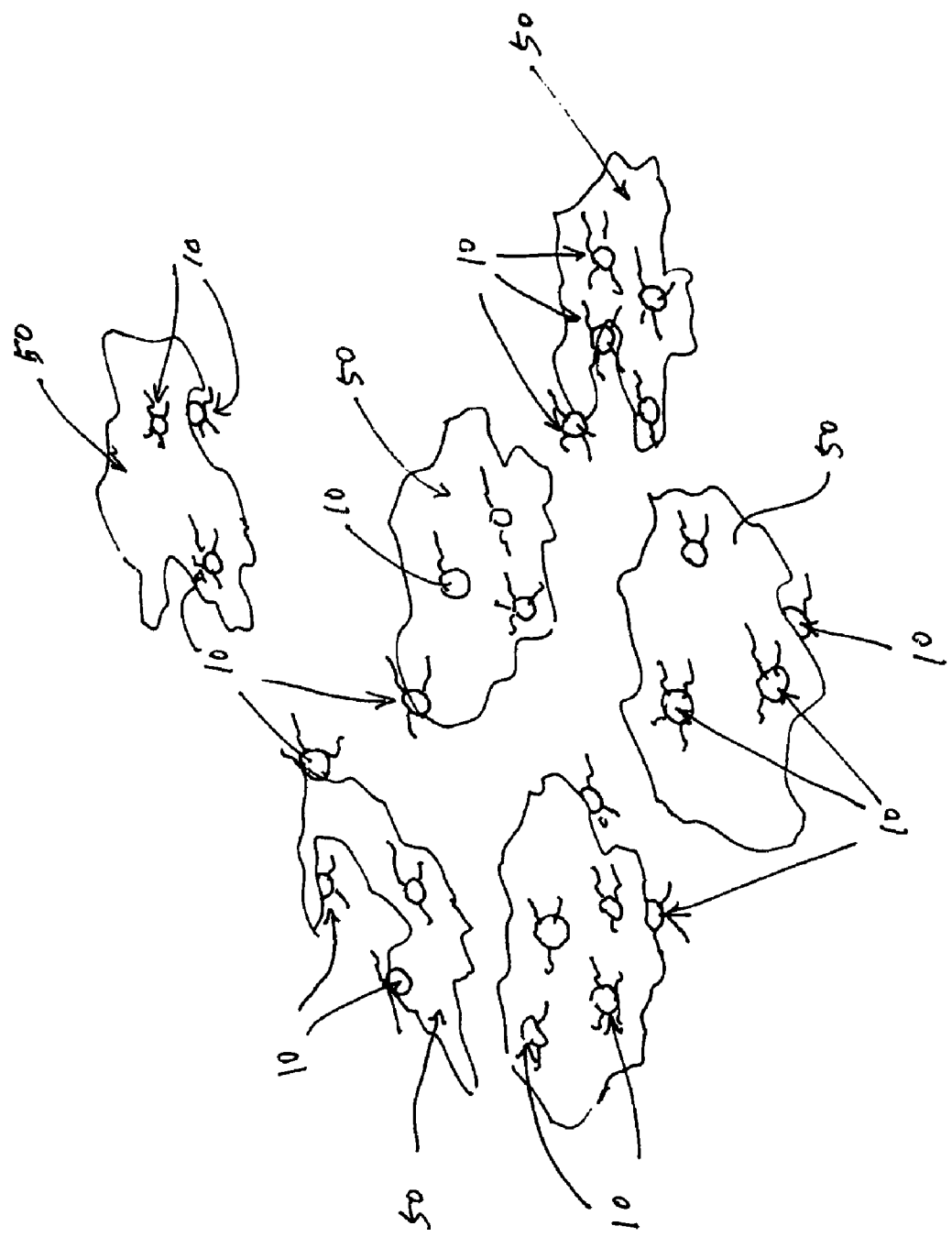
FIG. 2 is a schematic representation of a cellulose-based substrate or carrier 50, according to the present invention, that incorporates a metal-ion-coated high-surface area nanoparticles 10 material.

The present invention relates to an odor-control delivery mechanism that can be employed independently by itself or as part of a product or article. The present invention builds upon previous advances and improves the use of a carrier vehicle for odor control applications. The delivery mechanism makes use of metal-modified nanoparticles, such as described in U.S. Patent Application Publication No. 2006/0008442, by MacDonald et al., the contents of which are incorporated herein by reference. "Nanoparticle" refers to a high surface material having a particle diameter of less than about 500 nanometers. The nanoparticles are combined with a substrate that has a physical form and texture of fine cellulose-based granules, such as described in International Patent Application No. WO 2006/048280, by Ozersky et al., which describes multi-functional surface-modified cellulose-containing fibers for use in making paper, tissue and cardboard products, and a process for manufacturing the granules. The contents of WO 2006/048280 are incorporated herein by reference.

The cellulose fibers according to the present invention are at least partially in the form of granules may be completely in the form of granules, essentially in the form of granules or a mixture of fibers and granules. Both the granules and the mixture are free-flowing, which is associated with the advantages described above. The granules can be described as "saw-dust-like" or have a consistency like that of confectionary sugar. The granules tend to be irregularly shaped and have an average gross dimension in the range of about 20-3000 micrometers (μm). According to a preferred embodiment of the present invention, the particles in the granules have a diameter of 150 to 2500 μm. Typically, the granules range between about 200 or 700 μm to about 1200 μm or 1500 μm. It is especially preferable for them to have a diameter of 400-500 μm. The granules are constituted with a porous cellulose-based body or substrate having a high-surface area of at least about 200 $m^2$/gram of material. An average powder density of the granules (measured according to DIN 53,468) of 30 to 600 g/l is also preferred. An average powder density of 100-300 g/l.+–0.15% is especially preferred here. For example, the granules may be granules of the product Vitacel LC 200, cellulose fibers from the company J. Rettenmaier & Sohne GmbH Co. [J. Rettenmaier and Sons Inc.], Germany.

Various kinds of natural fibers may be used in the making of the granules, such as wood pulp fibers, corn silk, hemp, flax or cotton fibers, or other plant cellulose. Cellulose fibers obtained from wood and at least partially in the form of granules are preferred. Other suitable plant fibers comprise, for example, apple fibers, orange fibers and wheat fibers. Those skilled in the art will be familiar with methods of producing cellulose fibers from wood and/or other plant fibers so that they are at least partially in the form of granules. Metal-modified particles are either adhered to a surface, interfolded among, or encapsulated within or by the cellulose-based carrier substrate, such that each of the metal-modified particles has adsorbed metallic ions that are adapted to bind a molecule of a gaseous compound, an odorous compound, or combinations thereof. Hence, the granules function as a carrier vehicle for an odor control agent.

The cellulose-based granules have a structure suitable for suppressing odors. The cellulose fibers according to the present invention have advantages with regard to the amount of absorbent material to be used. In comparison with polyacrylates which are used as superabsorbers, the cost of the granules is approximately of the same order of magnitude as the cost of conventional cellulose.

In certain embodiments, the cellulose fibers of this invention can bee at least partially in the form of granules; these fibers will preferably have an average fiber length of about 100 μm to about 600 μm. An average fiber length of about 300 μm is especially preferred. According to a preferred embodiment of the present invention, the average fiber thickness of the fibers is about 10 μm to about 50 μm. An average fiber thickness of 20 μm is particularly desirable.

If the cellulose fibers, at a portion of which is in the form of granules, are in the form of a mixture of fibers and granules, this may be a "true" mixture, i.e., the cellulose fibers and the resulting granules are brought in contact and mixed by methods with which those skilled in the art are familiar. On the other hand, the mixture may also consist of particles which are in the form of granules, but fibers are present on the surface of the individual granule particles. Such "mixtures" can be produced by suppressing the process of winding fine cellulose fibers or granulating them to granules so promptly that individual unwound fibers or incompletely granulated fibers project out of the granules. The mixture of granules and fibers preferably includes from 10 wt % to 80 wt % fibers. It is especially preferred for the mixture to contain 60-70 wt % granules and 30 to 40 wt % fibers. In addition to the cellulose fibers the superabsorbers, superabsorbent materials in particle form, superabsorbent fibers, viscose staple fiber or synthetic staple beads of different lengths, polyolefins, such as polyethylene, or polystyrene, etc.

According to the present invention, the metal-modified silica particles are physically incorporated interstitial spaces between the cellulose fibers or adhered by electrostatics to the surfaces of the fibers. No chemical bonding is employed. Dosing the amount in a particular application can be made very flexible. Depending on the desired concentration of active agents associated with the granules one can easily adjust the amount of granules applied per dose. For instance, one can use about 500 mg of a granule sample doped at 10% active metal-modified particles to apply about 50 mg actives in a product. The cellulose-based granules having odor-control chemistry may be provided in a loose, free-flowing powder form in porous packaging that allows air to flow through and be reacted upon by the nanoparticles located on the cellulose substrates.

As described in the work by MacDonald et al., modified high surface area materials are useful in removing gaseous compounds and/or odorous compounds. "Gaseous compound" or "gas" includes any molecule or compound that can exist as a gas or vapor. "Odorous compound" or "odor" refers to any molecule or compound detectable to the olfactory system. Odorous compounds can exist as a gaseous compound and can also be present in other media such as liquid. The high surface area materials have at least one metal ion present on the surface of the high surface area material, and the metal ion creates an active site that binds with at least one gaseous compound and/or odorous compound thereby removing the compound from the surrounding environment. High surface area materials can also absorb certain gaseous compounds and/or odorous compounds from the surrounding environment by adsorption directly onto the surface area of the high surface area materials.

Gas and/or odor removing particles are modified high surface area materials. High surface area materials useful in this invention have a large surface area due to the small size of the individual particles of the high surface area material. High surface area materials useful in this invention have a suitable surface area of at least about 200 square meters/gram, more suitably about 500 square meters/gram, and more suitably about 800 square meters/gram.

While the invention will be described hereinafter with particular reference to nanoparticles, it will be understood that the invention is useful with various high surface area materials. FIG. 1 shows a modified nanoparticle 10 according to one embodiment of this invention, useful as a gas and/or odor removing particle. The modified nanoparticle 10 includes a nanoparticle 15 and metal ions 20. FIG. 1 shows a plurality of metal ions 20; however modified nanoparticle 10 can have various amounts of metal ions 20 and will have at least one metal ion 20. The modified nanoparticle 10 is useful for removing various gaseous compounds and/or odorous compounds. The specific compound to be removed is generally dependent on the specific metal ions 20 used and the type of nanoparticle 15.

Nanoparticles useful in the present invention may include, without limitation, silica, alumina, magnesium oxide, titanium dioxide, iron oxide, gold, zinc oxide, copper oxide, organic nanoparticles such as polystyrene, and combinations thereof. Nanoparticles are not generally ionic yet still have an overall electric Zeta Potential. "Zeta Potential" refers to the electrical potential, or electrokinetic potential, that exists across the interface of all solids and liquids. Nanoparticles with either positive or negative Zeta Potentials are known. Natural occurring chemical reactions on the surface of a nanoparticle result in the Zeta Potential of that nanoparticle. For example, silica nanoparticles are tetrahedral complexes of silicon dioxide molecules. On the surface of the silica particles the silicon dioxide molecules can undergo chemical reactions forming silanol groups (SiOH) the silanol groups reacting with other silanol groups to form siloxane bonds (Si—O—Si bonds). The dehydration reactions of the silanol groups to form the silanol bond and the reverse reactions result in a negative Zeta Potential and allow positively charged metal ions to adsorb onto the silica.

The nanoparticles useful in this invention will typically have a first Zeta Potential and a second Zeta Potential after adsorption of the metal ion onto the nanoparticle due to the addition of the oppositely-charged metal ions. The Zeta Potential change of the nanoparticle is related to the amount of metal ions adsorbed onto the nanoparticle. This relationship provides a measurement for determining the amount of adsorbed metal ions and a method for controlling the amount of adsorption. For instance, the addition of a dilute solution of copper chloride drop-wise to a silica nanoparticle solution until the Zeta Potential of the silica suspension changed from—25 millivolts to a higher Zeta Potential, such as in the range of about—5 millivolts to—15 millivolts, was found to be provide a sufficient concentration of metal ions adsorbed onto the nanoparticles to remove particular odorous compounds. In one embodiment of this invention the nanoparticle has a difference between the first and second Zeta Potential of at least about 1.0 millivolt and suitably at least about 5.0 millivolts.

The nanoparticles of this invention are modified with metal ions that ionically bond with compounds such as gases and odorous compounds. "Metal ion" refers to salt ions and/or ion complexes of transition metal elements designated as IB through VIIIB on the periodic table. Other ions can be used in the invention as well. Metal ions are adsorbed onto high surface area materials due to differences in electric potential. Positively charged metal ions are adsorbed onto a negatively charged surface of a nanoparticle and vice versa. Examples of metal ions useful in this invention include, without limitation, copper ion ($Cu^{+2}$), silver ion ($Ag^{+1}$), gold ion ($Au^{+1}$ and $Au^{+3}$), iron (II) ion ($Fe^{+2}$), iron (III) ion ($Fe^{+3}$), and combinations thereof In one embodiment of this invention, the modified nanoparticles include about 20-200 metal ions per nanoparticle, and typically and more desirably about 40-75 metal ions per nanoparticles.

In one embodiment of this invention the nanoparticle useful in this invention has a negative Zeta Potential and adsorbs positively charged metal ions. One suitable nanoparticle has a negative Zeta Potential of about—1 to—50 millivolts and suitably about—1 to—20 millivolts. In one embodiment of this invention the nanoparticle having a negative Zeta Potential is a silica nanoparticle. Silica nanoparticles useful in this invention are available from Nissan Chemical Industries, Ltd., Houston, Tex., under the name SNOWTEX®, have a particle size range of 1-100 nanometers. The silica nanoparticle can be modified with a positively charged metal ion such as copper ions, silver ions, gold ions, iron ions, and combinations thereof.

In another embodiment of this invention the nanoparticle useful in this invention has a positive Zeta Potential and adsorbs negatively charged metal ion complexes. One suitable nanoparticle has a positive first Zeta Potential of about 1 to 70 millivolts and suitably about 10 to 40 millivolts. In one embodiment of this invention the nanoparticle having a positive Zeta Potential is an alumina nanoparticle. Alumina nanoparticles are also available from Nissan Chemical Industries, Ltd., Houston, Tex., under the name ALUMINASOL®, and have size ranges of about 1-300 nanometers. The alumina nanoparticle can adsorb negatively charged metal ions and metal ion complexes such as permanganate ions.

Current odor control materials such as activated charcoal or sodium bicarbonate rely on the surface area to absorb certain odors. Using these materials is not as effective at odor removal as the modified high surface area materials of this invention. The addition of a metal ion adsorbed onto the surface of a nanoparticle, as in this invention, provides an active site for capturing and neutralizing gases and odorous compounds, such as sulfur, nitrogen, and/or oxygen containing compounds. In addition, the modified nanoparticles of this invention still have the large surface area that is useful in absorbing other odorous compounds. The metal ion active sites of the modified nanoparticles are particularly useful in removing odorous compound such as mercaptans, ammonia, amines, and mono-and disulfides. Other odorous compounds such as aliphatic ketones, carboxylic acids, aliphatic aldehydes, and aliphatic terpenoids can be removed by adsorption onto the large surface area of the modified nanoparticles. Modified nanoparticles are useful in removing odors caused by sulfides, disulfides, trisulfides, thiols, mercaptans, ammonia, amines, isovaleric acid, acetic acid, propionic acid, hexanal, heptanal, 2-butanone, 2-pentanone, 4-heptanone, and combinations thereof. Modified nanoparticles can also remove gases such as ethylene gas, carvone, dienals, and terpenoids.

More than one type of metal ion can be coated on a nanoparticle. This has an advantage in that certain metal ions may be better at removing specific gases and/or odorous compounds than other metal ions. In one embodiment of this invention more than one type of metal ion are adsorbed onto a nanoparticle for more effectively removing more than one type of gaseous compound or odorous compound from a medium. In one embodiment of this invention more than one type of metal ion are adsorbed onto a nanoparticle for removing at least one gaseous compound and at least one odorous compound from a medium.

Modified nanoparticles of this invention can be used in combination with other modified nanoparticles for effective removal of various gases and odors. In one embodiment of this invention copper ion modified silica nanoparticles are used in combination with permanganate ion modified magnesium oxide nanoparticles. By using the two different modified nanoparticles in combination, numerous odorous compounds can be removed. For example, the modified silica nanoparticle is useful for removing sulfur and amine odors and the modified magnesium oxide nanoparticle is useful in removing carboxylic acid odors. Combining modified nanoparticles of this invention allow for removal of a broader range of odors.

Modified nanoparticles are made by mixing nanoparticles with solutions containing metal ions. Such solutions are generally made by dissolving metallic compounds into a solvent resulting in free metal ions in the solution. The metal ions are drawn to and adsorbed onto the nanoparticles due to the electric potential differences. The Zeta Potential of a nanoparticle changes after the adsorption of metal ions according to this invention. Thus the Zeta Potential can be used to monitor the adsorption of metal ions onto the nanoparticle.

Modified high surface area materials according to this invention are versatile and can be used alone or in combination with other articles of manufacture for effective odor removal and control. Unlike activated charcoal deodorants, the modified nanoparticles of this invention maintain their odor neutralizing effects in solution. The modified nanoparticles of this invention also maintain odor neutralizing properties when dry and in aerosol form. This versatility allows for uses in various commercial products. Other advantages of the modified nanoparticles are that they are colorless in solution and white in powder form (activated charcoal is typically black). Modified high surface area materials of this invention can also be used in combination with other commercially available odor removal materials.

Modified nanoparticles of this invention can be applied to various substrate materials. In one embodiment of this invention modified nanoparticles are held onto a surface of a material by the electrical potential differences between the modified nanoparticle (Zeta Potential) and the material surface (Streaming Potential). Modified nanoparticles of this invention can be applied as a solution to a material surface and dried, resulting in a surface that absorbs gas and/or odors.

In one embodiment of this invention a substrate is treated with a modified high surface area material to provide or produce an odor absorbing article of manufacture. The modified high surface area material, such as a nanoparticle, includes at least one metal ion adsorbed onto the high surface area material. In an embodiment of a product that may incorporate the present odor control carrier vehicle, the product may be made with a substrate that is desirably a gas permeable material, such as, for example, a nonwoven web made from various and alternative polymers and/or natural fibers, a woven fabric, or a breathable film. Various and alternative nonwoven webs or fabrics are available for use as the substrate in this invention, such as, for example, airlaid webs, meltblown webs, spunbond webs, bonded carded webs, and/or coform webs, including those made from thermoplastic materials, such as polyolefins (e.g., polyethylene and polypropylene homopolymers and copolymers), polyesters, polyamines, and the like, or natural fibers such as wood pulp fibers, hemp, flax or cotton fibers, or other cellulose fibers.

According to another embodiment of the invention, one may incorporate the nanoparticles-doped or infused cellulose-based granules in an absorbent article, such as described in U.S. Patent Application Publication No. 2006/0229580 A1, by Raidel et al., the content of which is incorporated herein by reference. As used herein, the term "absorbent article" refers to products or articles suitable for absorption, in particular for absorption of body fluids. This includes in particular the absorption of urine, blood and fecal matter. Absorbent articles, according to the present invention, are often disposable articles, but they need not necessarily be disposable. Examples of absorbent articles according to the present invention include sanitary pads, in particular sanitary napkins and panty liners, diapers, incontinence pads, bandages and similar articles.

An example of a technique for applying or dosing the present cellulose-based granules as a delivery mechanism in personal care products or other absorbent articles is described in detail in U.S. Patent Application Publication No. 2007/0100304 A1, by Fell et al., the content of which is incorporated herein by reference. Fell et al. describe a method for incorporating odor control agent particles into an absorbent article, in which odor control particles are "homogenously" distributed (e.g., in a substantially uniform manner) within an air-formed pulp fiber matrix of an absorbent core of an absorbent article. An absorbent core containing such a homogeneously distributed odor control particles may possess a greater surface area for contacting malodorous compounds, thereby increasing the likelihood of odor reduction.

Section II—Examples

The following examples illustrate the functionality of the carrier vehicle according to the present invention.

Granular cellulose particles prepared by J. Rettenmaier & Sons are physically blended to incorporated metal-based odor control chemistries. All the particles were based on Vitacel LC 200 (fiber size of 300 microns, 75-95 g/l bulk density). The chemistries tested included iron coated silica particles (FeOXS, ratio of iron:silica=100:1), which has been proven to reduce malodors in a human sensory test panel The particles prepared included both 2.5 and 5% loading of the FeOXS. The odor removal ability of the particles was assessed by gas chromatography (GC) headspace experiments with model odorants. Cellulose samples were weighed and placed in GC headspace vials. Ethyl mercaptan (EtSH, 2.4 µl, 2.0 mg) or triethylamine (TEA, 3.0 µl, 2.2 mg) was added to a vial, the vial was covered with a cap and crimped shut. This was repeated for each vial. Three odorant control samples were run among the samples to create a reference set. Three reference samples of Vitacel LC 200 and FeOXS were also included to measure the amount of odor absorbed by the substrate and pure compounds themselves. The GC are equipped with a headspace analyzer, a DB-624 column, and an FID detector (temp=250° C.). Samples are equilibrated for 10 minutes at 37° C. in the headspace analyzer prior to injection into an 85° C. loop. Injection onto the 30° C. column (EtSH) or 100° C. column (TEA) occurs at 105° C. with a run time of 5 minutes.

The active concentrations in the various particles are summarized in Table 1. All the particles were based on Vitacel LC 200 (fiber size of 300µ, 75-95 g/l bulk density). The chemistries tested included iron coated silica particles (FeOXS, ratio of iron:silica=100:1) and anthraquinone dyes acid green 25 and remazol brilliant blue R, all of which have been proven to reduce malodors in the ORP setting.

TABLE 1

Details of particles according to the present invention, based on Vitacel LC 200 and contain odor control chemistries.

| Particle ID | Active component |
|---|---|
| FeOXS 5% | 5% iron coated silica at 100:1 Fe:Si |
| FeOXS 2.5% | 2.5% iron coated silica at 100:1 Fe:Si |

The experimental results suggest that particles containing FeOXS performed well removing both triethylamine and EtSH under the experimental conditions, indicating that the ability of the FeOXS to remove the odorant was not compromised by delivery on the particles. The data suggests that the loading of the FeOXS on the particles (5% vs. 2.5%) had an impact on the total amount of odorant removed, as expected.

Figure 3:
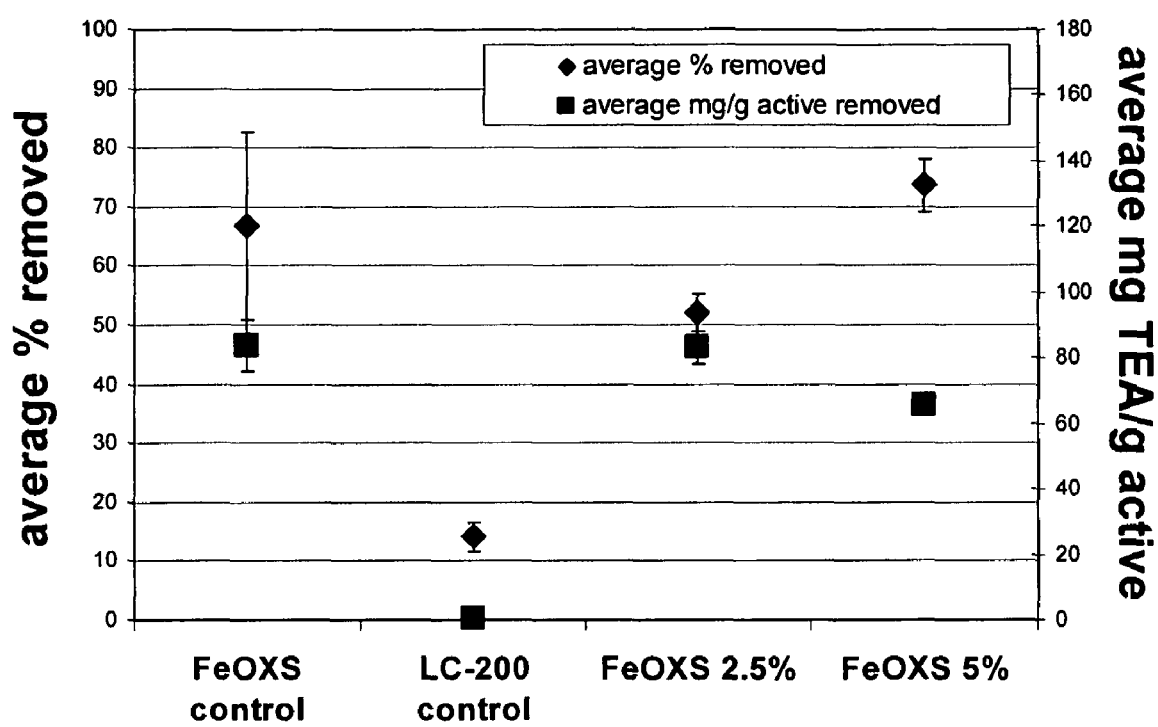
FIG. 3, is a graph showing the plot of average % removed (♦) and average amount (mg/g) removed (■) vs. the odorant granule samples containing control technologies exposed to triethylamine (3.0 µl).
Figure 4:
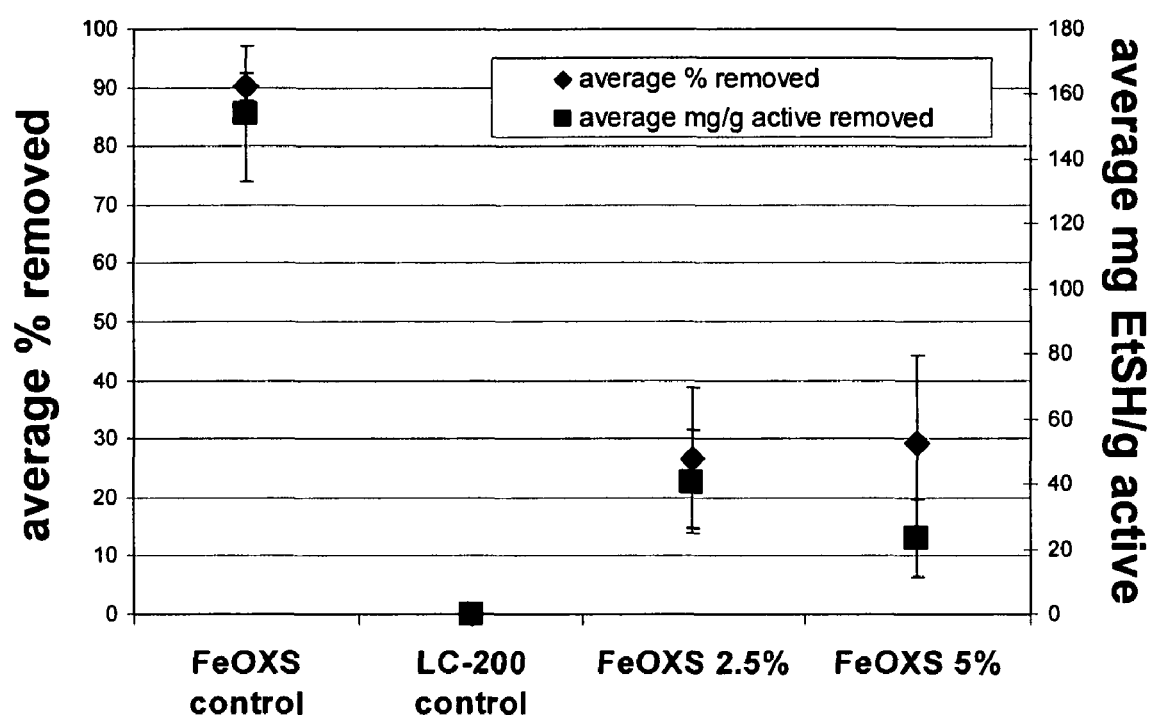
FIG. 4, is a graph showing the plot of average % removed (♦) and average mg/g removed (■) vs. the various odorant granule samples containing odor control technologies exposed to ethyl mercaptan (2.4 µl).

FIG. 3 details the results of the GC headspace obtained for the particles exposed to TEA. FIG. 4 contains the results when the particles are exposed to EtSH. The percentage odorant removed (◆(TEA), ◆(EtSH)) was not corrected for the absorption by the LC 200 substrate itself, but in both cases the control substrate removes about 10% odorant. The amount of (mg) odorant removed per amount (g) active (■(TEA), ■(EtSH)) is calculated based on the theoretical loading of the active on the particles to allow for direct comparison to the pure control samples.

Although the present invention has been described generally and in detail by way of examples and the accompanying figures, persons of skill in the art will understand that the invention is not necessarily limited to the particular embodiments, but that modifications and variations may be made without departing from the spirit and scope of the invention defined by the following claims.

We claim:

1. An odor control granule comprising a porous cellulose-based carrier substrate having high-surface area, metal-modified silica particles either adhered to or encapsulated within said carrier substrate, wherein each of said metal-modified silica particles has adsorbed metallic ions that are adapted to bind a molecule of a gaseous compound, an odorous compound, or combinations thereof.

2. The odor control granule according to claim 1, wherein a number of said cellulose-based carrier substrates is free-flowing and do not exhibit a tendency to agglomerate to each other.

3. The odor control granule according to claim 1, wherein said carrier substrate has a surface area greater than 200 $m^2$/gram.

4. The odor control granule according to claim 1, wherein said cellulose-based carrier substrate has an average diameter of about 200-700 μm.

5. The odor control granule according to claim 1, wherein a number of said cellulose-based carrier substrates exhibit powder-like characteristics, wherein the granules have an average powder density of 30 to 600 g/l according to DIN 53,468.

6. The odor control granule according to claim 5, wherein the granules have an average powder density according to DIN 53,468 amounting to 100 to 300 g/l.+−0.15%.

7. The odor control granule according to claim 1, wherein cellulose fibers are present at least partially in the form of granules are partially also present in the form of fibers.

8. The odor control granule according to claim 7, wherein said cellulose fibers have an average fiber length of about 100 μm to about 600 μm.

9. The odor control granule according to claim 8, wherein said cellulose fibers have an average fiber length of about 300 μm.

10. The odor control granule according to claim 8, wherein said cellulose fibers have an average fiber thickness of about 10 μm to about 50 μm.

11. The odor control granule according to claim 8, wherein said cellulose fibers have an average fiber thickness of about 20 μm.

12. The odor control granule according to claim 8, wherein said cellulose fibers used to produce the granules are fine fibers, preferably fibers with an average fiber length of about 100 to 600 μm and an average fiber thickness of about 10 to 50 μm.

13. The odor control granule according to claim 1, wherein said odorous compound comprises: a compound selected from the group consisting of sulfur-containing compounds, nitrogen-containing compounds, oxygen-containing compounds, and combinations thereof.

14. The odor control granule according to claim 1, wherein said porous cellulose-based carrier substrate includes a synthetic polymer material.

15. The odor control granule according to claim 1, wherein said metal-modified silica particles each have a surface area of at least about 170 square meters/gram.

16. The odor control granule according to claim 1, wherein said metal-modified silica particles each have a surface area of at least about 200 square meters/gram.

17. The odor control granule according to claim 1, wherein said metal-modified silica particle is formed from silica, alumina, magnesium oxide, titanium dioxide, iron oxide, gold, zinc oxide, copper oxide, polystyrene, or combinations thereof.

18. The odor control granule according to claim 1, wherein said metallic ions includes an ion selected from one of the following metals: copper, iron, manganese, cobalt, nickel, or a combination thereof.

19. The odor control granule according to claim 1, wherein said metal-modified silica particle is iron-coated (FeOXS), copper-coated (CuOXS), or a combination thereof.

20. A carrier vehicle for an odor control agent comprising: a porous cellulose-based substrate having a high-surface area of at least about 200 $m^2$/gram, metal-modified silica particles either adhered to or encapsulated within said cellulose-based substrate, wherein each of said metal-modified silica particles has adsorbed metallic ions that are adapted to bind a molecule of a gaseous compound, an odorous compound, or combinations thereof.

21. The carrier vehicle according to claim 20, wherein said cellulose-based carrier substrate has a mean cross-sectional size ranging from about 150 μm to about 2500 μm.

22. The carrier vehicle according to claim 21, wherein a number of said cellulose-based carrier substrates remains free-flowing and do not exhibit a tendency to agglomerate to each other.

23. The carrier vehicle according to claim 21, wherein said odorous compound comprises: a compound selected from the group consisting of sulfur-containing compounds, nitrogen-containing compounds, oxygen-containing compounds, and combinations thereof.

24. The carrier vehicle according to claim 21, wherein said porous cellulose-based carrier substrate also includes a synthetic polymer component.

25. The carrier vehicle according to claim 21, wherein said metal-modified silica particles are physically incorporated in interstitial spaces between cellulose fibers or adhered by electrostatics to a surface of said cellulose fibers.

26. The carrier vehicle according to claim 25, wherein no chemical bonding is employed.

27. The carrier vehicle according to claim 21, wherein said cellulose-based substrate is doped at 10% concentration of active metal-modified particles.

28. The carrier vehicle according to claim 27, wherein said metal-modified silica particles each have a surface area of at least about 170 square meters/gram.

29. The carrier vehicle according to claim 21, wherein said metal-modified silica particle is formed from silica, alumina, magnesium oxide, titanium dioxide, iron oxide, gold, zinc oxide, copper oxide, polystyrene, or combinations thereof.

30. The carrier vehicle according to claim 21, wherein said metallic ions includes an ion selected from one of the following metals: copper, iron, manganese, cobalt, nickel, or a combination thereof.

31. The carrier vehicle according to claim 21, wherein said metal-modified silica particle is an iron-coated (FeOXS), copper-coated (CuOXS), or a combination thereof.

32. An article of manufacture comprising an odor control granule having a porous cellulose-based carrier substrate having a high-surface area of at least about 200 $m^2$/gram, metal-modified particles either adhered to or encapsulated within said cellulose-based substrate, wherein each of said metal-modified silica particles has adsorbed metallic ions that are adapted to bind a molecule of a gaseous compound, an odorous compound, or combinations thereof.

33. The article of manufacture according to claim 32, wherein said article is a personal care or absorbent article.

34. The article of manufacturer according to claim 33, wherein said article is a feminine hygiene product, a diaper, an adult incontinence product, or a protective garment.

35. The article of manufacturer according to claim 33, wherein said article is an air-freshener medium or package, air-filter medium.

36. The article of manufacture according to claim 33, wherein said article is nonwoven fabric constructed medium having said cellulose-based carrier substrates in interstial spaces of said nonwoven fabric.

* * * * *